United States Patent [19]

Franklin

[11] Patent Number: 5,281,743

[45] Date of Patent: Jan. 25, 1994

[54] UNCATALYZED SYNTHESIS OF SYMMETRICAL DICARBONATES

[75] Inventor: Ralph Franklin, Danbury, Conn.

[73] Assignee: Akzo N.V., Arnhem, Netherlands

[21] Appl. No.: 30,759

[22] Filed: Mar. 12, 1993

[51] Int. Cl.$^5$ ................... C07C 68/04; C07C 69/96
[52] U.S. Cl. .................................................. 558/276
[58] Field of Search ........................................ 558/276

[56] References Cited

U.S. PATENT DOCUMENTS

| | | | |
|---|---|---|---|
| 3,496,209 | 2/1970 | Boudakian | 260/453 |
| 4,929,748 | 5/1990 | Franklin | 558/276 |
| 4,983,320 | 1/1991 | Franklin et al. | 252/350 |
| 5,030,664 | 7/1991 | Franklin et al. | 521/129 |
| 5,086,083 | 2/1992 | Franklin et al. | 521/129 |
| 5,151,541 | 9/1992 | Joerg et al. | 558/277 |
| 5,151,542 | 9/1992 | Kurimoto et al. | 558/277 |

FOREIGN PATENT DOCUMENTS

| | | |
|---|---|---|
| 1483560 | 6/1967 | France . |
| 2220564 | 10/1974 | France . |
| 46-06895 | 2/1971 | Japan ................... 558/276 |

OTHER PUBLICATIONS

Chemicals and the Environment Symposium, Chemspec. Meeting, Fall 1992, New Brunswick, NJ.
Journal of Organic Synthesis, vol. 27, pp. 1901–1902 (1962).

*Primary Examiner*—Mary C. Lee
*Assistant Examiner*—Michael G. Ambrose
*Attorney, Agent, or Firm*—Ralph J. Mancini; Louis A. Morris

[57] ABSTRACT

A dialkyl dicarbonate is prepared by contacting an alkyl haloformate with an alkali metal carbonate in the presence of a solvating amount of a solvent. The process of the invention does not require a catalyst, is easy to carry out, does not employ particularly hazardous materials, does not require cumbersome purification steps, and provides a high yield of dicarbonate.

19 Claims, No Drawings

UNCATALYZED SYNTHESIS OF SYMMETRICAL DICARBONATES

FIELD OF THE INVENTION

The present invention is generally related to an uncatalyzed process for the preparation of symmetrical dicarbonates.

BACKGROUND OF THE INVENTION

Dialkyl dicarbonates, also known as dialkyl pyrocarbonates, are useful as fermentation inhibitors in wines and fruit juices, as well as reagents in chemical synthesis. Several methods are known for preparing dialkyl dicarbonates, but these methods suffer from various disadvantages such as hazardous starting materials (e.g., phosgene), low yields, and time consuming and/or cumbersome purification steps.

In FR 1,483,460 (Shamshurin—Institut Khimii an Moldavskoisar, granted in 1967) alkyl chloroformate is reacted with potassium or sodium carbonate in the presence of a tertiary amine as a catalyst. While this method is in many respects an improvement over the prior art which proceeded it, it nonetheless is less than an ideal solution. In particular, the purification step necessary to separate the dialkyl dicarbonate from the tertiary amine is rather cumbersome, and the overall process has a disappointingly low yield.

U.S. Pat. No. 4,929,748 discloses a method of preparing dialkyl dicarbonate which comprises contacting an alkyl haloformate with an alkali metal carbonate in the presence of a catalytic amount of a crown ether and a solvating amount of a solvent.

French Publication No. 2,220,564 discloses a method of preparing dialkyl dicarbonate by carbonation of the corresponding alkali metal alcoholate in tetrahydrofuran followed by reaction with an excess of chloroformate. This method has the disadvantages of having to deal with large amounts of solvent and various hazardous and expensive materials such as metal alkoxides.

An article distributed at the "Chemicals and the Environment Symposium", held at the Fall 1992 Chemspec Meeting, (New Brunswick, N.J.), describes a process for the preparation of dialkyl and diaryl pyrocarbonates. The process generally comprises reacting a chloroformate with 50% sodium hydroxide in the presence of a catalyst without added solvent.

U.S. Pat. No. 5,151,542 discloses a process for the preparation of di-tertiary butyl dicarbonate which comprises reacting alkali metal tertiary butyl carbonate with methanesulfonyl chloride.

Prior art methods for preparing dialkyl dicarbonates suffer various drawbacks including problems arising from the use of toxic complexing agents or cosolvents, corrosion problems, unsatisfactory space-time yields, and problems incurred in working up the reacting mixture.

Accordingly, it is an object of the present invention to provide a process for preparing dialkyl dicarbonates which overcomes the disadvantages of the prior art and is safe, economical and provides high yields of the desired product.

SUMMARY OF THE INVENTION

The present invention generally relates to an uncatalyzed process for the preparation of dialkyl dicarbonates. More specifically, the process comprises reacting a alkyl haloformate with a alkali metal carbonate in acetonitrile, without the necessity of employing a catalyst. The present process is easy to carry out, employs less hazardous materials than many prior processes, does not involve cumbersome separation techniques and results in a relatively high yield.

DETAILED DESCRIPTION OF THE INVENTION

The present invention discloses an uncatalyzed process of preparing dialkyl dicarbonates which comprises reacting an alkyl haloformate with an alkali metal carbonate in a solvating amount of a liquid which will solvate the reactants, without the necessity of a catalyst. As with most systems, removal of the catalyst results in a greatly reduced reaction rate, or, no reaction at all. The present inventors have unexpectedly discovered, however, that certain chloroformates are sufficiently reactive as to require no catalyst in order to obtain complete reaction within an acceptable time, usually between eight (8) and twelve (12) hours.

The present invention unexpectedly provides high yields of dialkyl dicarbonates without the necessity of employing a catalyst, does not employ hazardous and/or expensive materials and is not plagued with extensive and costly purification techniques for catalyst residue removal.

The first component of the present process is an alkyl haloformate of the formula:

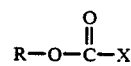

wherein X is halogen, and R is a straight or branched chain alkyl which is unsubstituted or substituted by one or more haloformate groups and/or which may have one or more linking functionalities. Preferred linking functionalities include oxygen, sulfur, carbonyl, aryl, cycloalkyl, and the like. R is preferably an alkyl with from 1 to 20 carbon atoms, more preferably 1 to 10 carbon atoms and still more preferably 2-8 carbon atoms. Examples of preferred alkyl moieties include but are not limited to ethyl, methyl, allyl, butyl, 2-ethylhexyl, isobutyl and alkyl. In a preferred embodiment, X is fluorine, chlorine, bromine or iodine. In a more preferred embodiment, X is fluorine, chlorine or bromine. In a most preferred embodiment, X is chlorine. Chloroformates derived from primary alcohols are preferred. Specific examples of preferred chloroformates include allyl chloroformate, isobutyl chloroformate, n-butyl chloroformate, 2-chloroethyl chloroformate, 2-ethylhexyl chloroformate, diethylene glycol bis-chloroformate, 1-4 butane diol bis-chloroformate and the like.

The synthesis of alkyl haloformates is well known to those of ordinary skill in the art, and most, especially those based upon chlorine, are commercially available.

The second component of the present process is an alkali metal carbonate of the formula:

wherein M is an alkali metal. In a preferred embodiment, M is sodium or potassium. In the most preferred embodiment, M is potassium. The alkali metal carbonate is preferably employed in finely divided form. These materials are well known and are commercially available.

The alkyl haloformate and alkali metal carbonate react together in a molar ratio of 2:1. It is therefore desirable that those reactants be present in approximately a 2:1 molar ratio. However, it can be advantageous to have a slight excess of alkali metal carbonate in order to ensure a reasonably short reaction time. It is preferred that the alkali metal carbonate be present at 45–300, more preferably 50 to 100 and still more preferably 55–60 mol % based on the alkyl haloformate.

Another component of the invention is a solvating amount of a liquid which will solvate the chloroformate. While many solvents will dissolve the chloroformates, a simple trial will determine if they are suitable in the process of the present invention. Materials which are operable in the present invention include acetonitrile, dichloromethane, toluene, tetrahydrofuran (THF), N,N-dimethylformamide (DMF) and the like. Of these solvents, acetonitrile is particularly preferred because of its extreme efficiency in providing a high yield in a relatively short time.

The reactants may be combined in any convenient manner, but it is preferred that certain procedures be followed in order to maximize yield. In particular, the presence of water is detrimental to the reaction and the use of anhydrous ingredients is therefore recommended. Further, it is recommended that the alkali metal carbonate and the solvent be added to the reaction vessel and stirred while the alkyl haloformate is slowly added. While the reaction is exothermic, i.e., the temperature of reaction will increase, higher temperatures will increase the reaction rate, but simultaneously increase the risk of undesired dialkyl monocarbonate formation as the reaction nears completion. Also, higher temperatures may lead to the thermal decomposition of the alkyl haloformates. Accordingly, the reaction temperature is preferably maintained between about $-30°$ C. to about $100°$ C., and still more preferred, between about $0°$ and $60°$ C. The total reaction time is typically between about 0.5 to 24 hours, with about 1 to 8 hours being preferred.

The invention will be further illustrated by the following non-limiting examples.

Example 1—Preparation of Diisobutyl Dicarbonate

Isobutyl chloroformate (136.76 g, 1.0 mol.) was added dropwise to a stirred mixture of powered, anhydrous potassium carbonate (77 g, 0.56 mol) in acetonitrile at such a rate as to maintain a reaction temperature of $40°$ C. The reaction mixture was stirred for six (6) hours at ambient temperature and then allowed to stand overnight prior to work-up. The crude product was purified by vacuum distillation, and the fraction collected between $58°$ and $62°$ C. at 0.05–0.10 mmHg was found to be di-isobutyl dicarbonate. YIELD=86.93 g=80%.

Example 2—Preparation of Bis(2-Chloroethyl) Dicarbonate

2-Chloroethyl chloroformate (14.3 g, 0.10 mol) was added over 30 minutes to a stirred mixture of powdered potassium carbonate (7.7 g, 0.56 mol) in acetonitrile (25 ml). A very mild exotherm raised the reaction temperature by $1°-2°$ C. above ambient. Stirring was continued for a further 2 hours. The product was isolated by filtering off the inorganic salts and stripping the solvent under reduced pressure. The resulting liquid product (11.0 g, 0.048 mol) was identified by n.m.r. and i.r. spectroscopy as being essentially bis(2-chloroethyl) dicarbonate. Yield 95%.

Example 3

In a series of experiments, a number of alkyl chloroformates were reacted with potassium carbonate at room temperature in accordance with the following procedure. The chloroformate (0.10 mol) was added dropwise over 35–40 minutes to a stirred suspension of powdered potassium carbonate (0.056 mol) and acetonitrile (25 ml). The reaction was conducted at ambient temperature and any exotherm controlled by the use of a cooling bath to ensure that the maximum temperature did not exceed $40°$ C. The reaction was stirred for six hours and then allowed to stand overnight.

The product was isolated by filtering off the inorganic solids and stripping off the acetonitrile under reduced pressure. The isolated product was then dissolved in methylene chloride and washed twice with water, dried over magnesium sulfate, filtered and stripped of solvent on a rotary evaporator. The isolated products were analyzed by NMR and product distribution data is compiled below.

a.) Di-2-Ethylhexyl Dicarbonate from 2-Ethylhexyl Chloroformate

Quantitative yield, pale yellow liquid, analysis by NMR showed approximately 3% 2-ethyl hexanol, 5% di-2-ethylhexyl monocarbonate and 92% di-2-ethylhexyl dicarbonate.

b.) Dibutyl Dicarbonate from n-Butyl Chloroformate

93% yield, pale yellow liquid, NMR analysis showed greater than 90% dibutyl dicarbonate and a small amount of dibutyl monocarbonate.

c.) Diallyl Dicarbonate from Allyl Chloroformate

Quantitative yield, pale yellow liquid, NMR showed approximately 90% diallyl dicarbonate and 10% diallyl monocarbonate.

We claim:

1. A method of preparing a dialkyl dicarbonate which comprises reacting:

(a) an alkyl haloformate of the formula

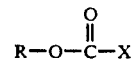

wherein: R is allyl or a $C_1$–$C_{20}$ straight or branched chain alkyl which is unsubstituted or substituted by one or more haloformate groups and which optionally may contain one or more linking groups selected from oxygen, sulphur, carbonyl, aryl, and cycloalkyl, and X is halogen, with (b) an alkali metal carbonate, in a solvating amount of liquid, with the proviso that a catalyst is not employed.

2. The method of claim 1 wherein said X of said haloformate is selected from the group consisting of fluorine, chlorine or bromine.

3. The method of claim 2 wherein X is chlorine.

4. The method of claim 1 wherein said R group of said alkyl haloformate is a $C_1$–$C_{10}$ alkyl group.

5. The method of claim 1 wherein said alkyl haloformate is selected from the group consisting of isobutyl chloroformate, 2-chloroethyl chloroformate, 2-ethylhexyl chloroformate, n-butyl chloroformate, allyl chloroformate, diethylene glycol bis-chloroformate, 1-4 butane diol bis-chloroformate and mixtures thereof.

6. The method of claim 1 wherein the solvent is selected from the group consisting of acetonitrile, dichloromethane, toluene, tetra-hydrofuran, and dimethylformamide.

7. The method of claim 5 wherein said solvent is acetonitrile.

8. The method of claim 1 wherein the alkali metal carbonate is a carbonate of lithium, sodium, or potassium.

9. The method of claim 7 wherein the alkali metal carbonate is a carbonate of potassium or sodium.

10. The method of claim 1 wherein the alkali metal carbonate is a carbonate of potassium, said alkyl haloformate is isobutyl chloroformate and the solvent is acetonitrile.

11. The method of claim 1 wherein the alkali metal carbonate is present at 45 to 300 mole % based on the alkyl haloformate.

12. The method of claim 10 wherein the alkali metal carbonate is present at 50 to 100 mole % based on the alkyl haloformate.

13. The method of claim 11 wherein the alkali metal carbonate is present at 55 to 60 mole % based on the alkyl haloformate.

14. The method of claim 1 wherein the reaction takes place at a temperature of from about $-30°$ to $100°$ C.

15. The method of claim 1 wherein the reaction takes place at a temperature from about $0°$ to $60°$ C.

16. The method of claim 1 wherein the reaction takes place in about 0.5 hours to about 24 hours.

17. The method of claim 1 wherein the reaction takes place in about 1 hour to about 8 hours.

18. The method of claim 1 wherein said alkyl haloformate is selected from the group consisting of isobutyl chloroformate and allyl chloroformate, said alkali metal carbonate is selected from the group consisting of sodium carbonate and potassium carbonate, and said solvent is acetonitrile.

19. A method of preparing a dialkyl dicarbonate which comprises reacting:
(a) an alkyl haloformate selected from the group consisting of isobutyl chloroformate, 2-ethylhexyl chloroformate, 2-chloroethyl chloroformate, n-butyl chloroformate, and allyl chloroformate, with
(b) potassium carbonate in a solvating amount of acetonitrile, with the proviso that a catalyst is not employed.

* * * * *